(12) United States Patent
Sogard et al.

(10) Patent No.: US 7,597,775 B2
(45) Date of Patent: *Oct. 6, 2009

(54) GREEN FLUOROPOLYMER TUBE AND ENDOVASCULAR PROSTHESIS FORMED USING SAME

(75) Inventors: David J. Sogard, Edina, MN (US); Jason P. Hill, Brooklyn Park, MN (US); Timothy S. Girton, Maple Grove, MN (US); Christopher B. Brodeur, Andover, MN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 35 days.

This patent is subject to a terminal disclaimer.

(21) Appl. No.: 10/012,919

(22) Filed: Oct. 30, 2001

(65) Prior Publication Data
US 2003/0082324 A1    May 1, 2003

(51) Int. Cl.
*B32B 37/00*    (2006.01)
(52) U.S. Cl. .............. 156/294; 156/293; 156/244.11
(58) Field of Classification Search .............. 156/293, 156/294, 244.13, 244.11; 623/1.13, 23.7, 623/23.71
See application file for complete search history.

(56) References Cited

U.S. PATENT DOCUMENTS

| | | | |
|---|---|---|---|
| 3,260,774 A | 7/1966 | Harlow | |
| 3,953,566 A | 4/1976 | Gore | |
| 4,208,745 A | 6/1980 | Okita | |
| 4,225,547 A | 9/1980 | Okita | |
| 4,250,138 A * | 2/1981 | Okita | 264/568 |
| 4,333,906 A * | 6/1982 | Porter et al. | 264/40.3 |
| 4,380,520 A * | 4/1983 | Taylor | 264/40.3 |
| 4,482,516 A | 11/1984 | Bowman et al. | |
| 4,547,142 A | 10/1985 | Arenhövel et al. | |
| 4,588,461 A * | 5/1986 | Braun | 156/143 |
| 4,655,771 A | 4/1987 | Wallsten | |
| 4,743,480 A | 5/1988 | Campbell et al. | |
| 4,791,966 A | 12/1988 | Eilentropp | |
| 4,828,770 A | 5/1989 | Fabian et al. | |
| 4,850,999 A | 7/1989 | Planck | |

(Continued)

FOREIGN PATENT DOCUMENTS

DE    39 18 736 A1    12/1990

(Continued)

OTHER PUBLICATIONS

Search Report issued on Dec. 5, 2002 for International Application No. PCT/US 02/27307.

*Primary Examiner*—Jeff H Aftergut
(74) *Attorney, Agent, or Firm*—Vidas, Arrett & Steinkraus, P.A.

(57) ABSTRACT

The present invention is directed to a green fluoropolymer tube which has a wall thickness of about 250 microns or less, preferably about 200 microns or less, and more preferably about 125 microns or less. With such thinness, the green tube may be formed into a tube of expanded fluoropolymer having a wall thickness of about 250 microns or less, preferably about 200 μm or less and more preferably about 125 microns or less. Such an expanded fluoropolymer tube is particularly well-suited for use as an endovascular prosthesis, such as a graft, or in a stent-graft, because of its flexibility and strength.

28 Claims, 8 Drawing Sheets

U.S. PATENT DOCUMENTS

| | | | |
|---|---|---|---|
| 4,911,846 A * | 3/1990 | Akasu et al. | 210/645 |
| 4,925,710 A | 5/1990 | Buck et al. | |
| 4,954,126 A | 9/1990 | Wallsten | |
| 4,971,836 A * | 11/1990 | Fukasawa et al. | 427/235 |
| 5,024,671 A * | 6/1991 | Tu et al. | 623/1.54 |
| 5,061,275 A | 10/1991 | Wallsten et al. | |
| 5,064,435 A | 11/1991 | Porter | |
| 5,071,407 A | 12/1991 | Termin et al. | |
| 5,112,900 A | 5/1992 | Buddenhagen et al. | |
| 5,123,917 A | 6/1992 | Lee | |
| 5,147,385 A | 9/1992 | Beck et al. | |
| 5,156,785 A | 10/1992 | Zdrahala | |
| 5,197,976 A | 3/1993 | Herweck et al. | |
| 5,221,261 A | 6/1993 | Termin et al. | |
| 5,234,456 A | 8/1993 | Silvestrini | |
| 5,282,823 A | 2/1994 | Schwartz et al. | |
| 5,282,824 A | 2/1994 | Gianturco | |
| 5,378,239 A | 1/1995 | Termin et al. | |
| 5,505,887 A | 4/1996 | Zdrahala et al. | |
| 5,591,226 A | 1/1997 | Trerotola et al. | |
| 5,607,468 A | 3/1997 | Rogers et al. | |
| 5,607,478 A | 3/1997 | Lentz et al. | |
| 5,609,624 A | 3/1997 | Kalis | |
| 5,620,763 A * | 4/1997 | House et al. | 428/36.9 |
| 5,628,782 A | 5/1997 | Myers et al. | |
| 5,628,786 A | 5/1997 | Banas et al. | |
| 5,628,788 A | 5/1997 | Pinchuk | |
| 5,639,408 A | 6/1997 | King et al. | |
| 5,641,443 A | 6/1997 | Calcote et al. | |
| 5,645,559 A | 7/1997 | Hachtman et al. | |
| 5,653,745 A * | 8/1997 | Trescony et al. | 623/23.71 |
| 5,667,523 A | 9/1997 | Bynon et al. | |
| 5,700,285 A | 12/1997 | Myers et al. | |
| 5,718,973 A | 2/1998 | Lewis et al. | |
| 5,735,892 A | 4/1998 | Myers et al. | |
| 5,749,880 A | 5/1998 | Banas et al. | |
| 5,788,626 A | 8/1998 | Thompson | |
| 5,800,522 A * | 9/1998 | Campbell et al. | 128/898 |
| 5,810,870 A | 9/1998 | Myers et al. | |
| 5,843,166 A | 12/1998 | Lentz et al. | |
| 5,874,032 A | 2/1999 | Zdrahala et al. | |
| 5,955,016 A | 9/1999 | Goldfarb | |
| 5,965,074 A | 10/1999 | Aubertin et al. | |
| 5,993,489 A | 11/1999 | Lewis et al. | |
| 6,001,125 A * | 12/1999 | Golds et al. | 623/23.7 |
| 6,027,779 A | 2/2000 | Campbell et al. | |
| 6,048,484 A | 4/2000 | House et al. | |
| 6,050,805 A | 4/2000 | Lupke | |
| 6,187,054 B1 | 2/2001 | Colone et al. | |
| 6,224,803 B1 | 5/2001 | Tiernan | |
| 6,264,684 B1 * | 7/2001 | Banas et al. | 623/1.13 |
| 6,537,471 B2 * | 3/2003 | Swanson et al. | 264/40.6 |
| 7,425,291 B2 * | 9/2008 | Venditti et al. | 264/150 |

FOREIGN PATENT DOCUMENTS

| | | |
|---|---|---|
| EP | 351584 A1 * | 1/1990 |
| EP | 0 551 179 A1 | 7/1993 |
| EP | 0 621 015 A1 | 10/1994 |
| GB | 1 505 591 | 3/1978 |
| WO | WO 87/04935 | 8/1987 |
| WO | WO 95/05131 | 2/1995 |
| WO | WO 95/05132 | 2/1995 |
| WO | WO 95/05555 | 2/1995 |
| WO | WO 96/00103 | 1/1996 |
| WO | WO 96/28115 | 9/1996 |
| WO | WO 96/40001 | 12/1996 |
| WO | WO 97 02791 A1 | 1/1997 |
| WO | WO 97/07751 | 3/1997 |
| WO | WO 98 38947 A | 9/1998 |
| WO | WO 01 15633 A | 3/2001 |
| WO | WO 02 41804 A | 5/2002 |

\* cited by examiner

GREEN FLUOROPOLYMER TUBE AND ENDOVASCULAR PROSTHESIS FORMED USING SAME

FIELD OF THE INVENTION

The present invention relates generally to a vascular prosthesis that is used to repair and/or replace or otherwise treat a vascular defect. More particularly, the present invention relates to an expandable prosthesis that incorporates extruded tubular members having minimal wall thickness. Such thin-walled tubular members permit construction of graft and stent-graft devices having very small outer diameters that are able to navigate tortuous vasculature without compromising structural integrity.

BACKGROUND OF RELATED TECHNOLOGY

Techniques have been developed in the prior art to form thin-walled polytetrafluoroethylene (PTFE) tubes. For example, U.S. Pat. No. 4,925,710 to Buck et al., discloses a method of coating a core with PTFE, wherein, after sintering, the PTFE coating is removable from the core to form a tube. Automotive cables and medical catheters are disclosed as useful products. No disclosure is provided for uniformity of wall thickness nor the production of the tubes in the absence of the core. Tubes having wall thicknesses of 0.002 inches (0.051 mm) and less, which are formed on solid cores, are disclosed.

Other techniques have been developed in the prior art where porous expanded PTFE (ePTFE) is prepared in tape or film form, and rolled or wrapped into tubular form with overlapping edges being bonded and/or sintered. See, e.g., U.S. Pat. No. 4,791,966 to Eilentropp (discloses wrapping a PTFE tape about a mandrel); U.S. Pat. No. 6,027,779 to Campbell et al. (discloses overlaying two pieces of ePTFE film in forming a tube). Although these methods have produced thin-walled tubes having wall thicknesses of 300 μm and less, these thin-walled tubes are formed of ePTFE and are not susceptible to further expansion (and thus further wall reduction). In addition, these tubes include one or more seams.

With typical prior art PTFE tube extrusion, a PTFE billet is pre-formed and loaded into a ram extruder, resulting in a relatively thick-walled tube extrudate (typically having a wall thickness in the range of 0.010-0.017 inches (standard green tube for vascular graft)). Although the extrudate may be slightly tensioned during take-up after extrusion, the extruded tube is "green". (As used herein, a "green" fluoropolymer tube, such as a PTFE tube, is unsintered and either unexpanded or minimally expanded due to the manufacturing process such as, e.g., being subjected to tension during take-up after extrusion.) In addition, extruded green PTFE typically contains a lubricant, which is volatilized. Thereafter, the tube may be subjected to further processes, including heating, sintering and expansion, with expansion resulting in reducing the thickness of the tube wall to a range of about 0.010 to about 0.017 inches, with a range of about 100% to about 500% elongation. As a result, a seamless, thin-walled tube of ePTFE may be formed.

Conventional PTFE extrusion methods have had difficulty in producing thin-walled tubes for use as medical implants, such as vascular prostheses. For example, U.S. Pat. Nos. 5,700,285; 5,735,892 and 5,810,870 to Myers describe these difficulties, including the difficulty of maintaining the uniformity of wall thickness of thin-walled extruded PTFE tubes. Consequently, these patents are directed to producing thin-walled vascular tubes using thin PTFE sheets which are wrapped to form a tube.

SUMMARY OF THE INVENTION

To overcome deficiencies of the prior art, a green fluoropolymer tube is provided having a wall with a generally uniform thickness in the range of about 250 μm or less, preferably about 200 μm or less, and, more preferably, about 125 μm or less. Advantageously, from such a thin-walled green tube, a tube of expanded fluoropolymer can be formed having a wall thickness in the range of about 250 μm or less, preferably about 200 μm or less, and more preferably about 125 μm or less.

In a preferred embodiment, the green fluoropolymer tube is extruded, and therefore, is seamless. Accordingly, a seamless expanded fluoropolymer tube, i.e. ePTFE is also formed from the green tube and is particularly well-suited for forming a prosthetic member, particularly, an endovascular prosthetic member, such as a graft. In addition, the prosthetic member can include multiple concentric layers of such tubes and can be used in combination with stents to form a stent-graft, i.e., wherein a distensible member, such as a balloon-expandable or a self-expanding stent, is attached to or otherwise integrated with the graft for structural support. It is preferred that the fluoropolymer be PTFE due to its inert, biologically-compatible, and porous characteristics.

Because of the thinness of the extruded green fluoropolymer tube, precise extrusion equipment is required, such as that disclosed in copending U.S. application Ser. No. 10/012,825, which is also assigned to the assignee herein. Although other apparatuses may be used, it must be noted that due to the thinness of the green tube, it does not have inherent structural strength and integrity to support itself in a hollow state, i.e., to maintain its lumen open and avoid kinking and collapsing, in whole or in part, when the green tube is "wet" immediately after being extruded. To provide support, a pressurized stable medium, preferably air, is injected into the lumen during extrusion to provide support.

In one particularly desirable aspect of the invention there is included a stent-graft device which includes concentric tubular layers of extruded thin-wall green PTFE which has been expanded and which incorporate a stent between the concentric layers. The concentric tubular layers are desirably laminated together by heat, adhesive or other means, desirably through the openings in the stent. Alternatively, each layer may be adhered independently to the stent.

These and other features of the invention will be better understood through a study of the following detailed description and accompanying drawings.

DETAILED DESCRIPTION OF THE PREFERRED EMBODIMENT

One aspect of the present invention is directed to a green fluoropolymer tube which has a wall thickness of about 250 µm or less, preferably about 200 µm or less, and more preferably about 125 µm or less. With such thinness, the green tube may be formed into a tube of expanded fluoropolymer having a wall thickness of about 250 µm or less, preferably about 200 µm or less, and more preferably about 125 µm or less. Such an expanded fluoropolymer tube is particularly well-suited for use as an endovascular prosthesis, such as a graft, or in a stent-graft, because of its flexibility and strength.

Now referring to the figures, wherein like elements are identically numbered, the configuration and operation of the present invention can be described.

Figure 1:
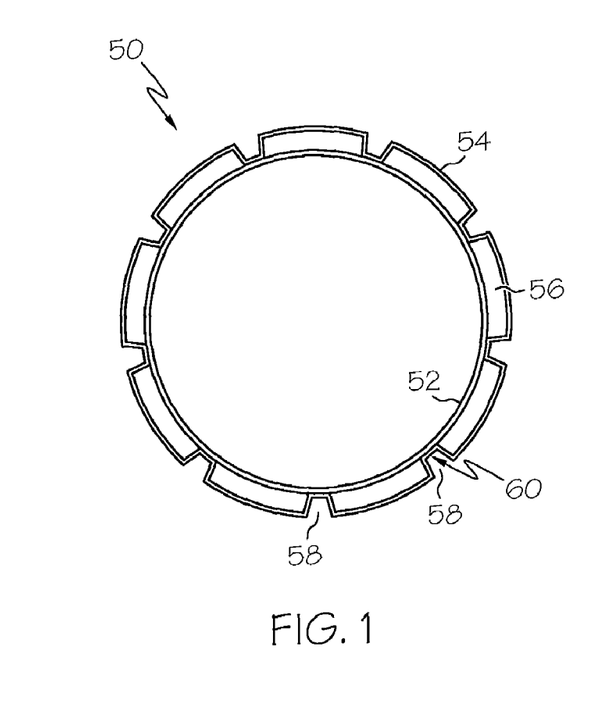
FIG. 1 is an end view of a prosthesis formed in accordance with the subject invention.
Figure 2:
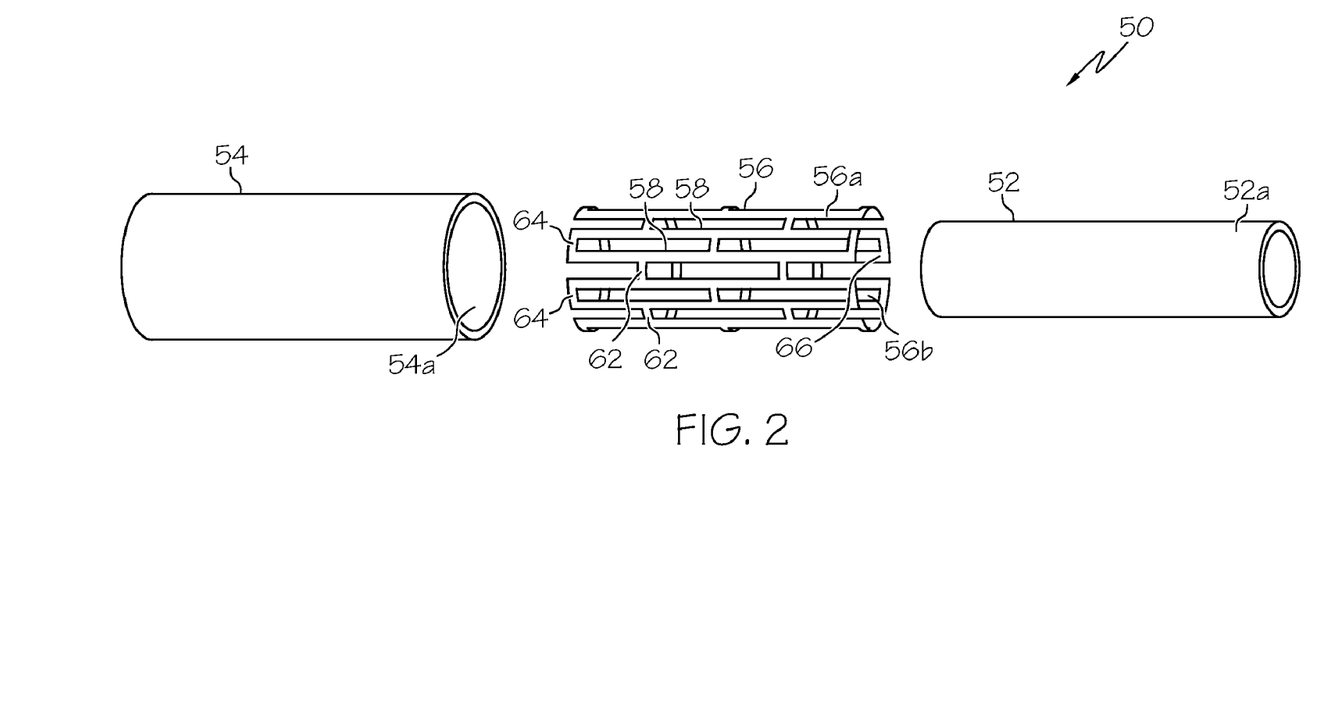
FIG. 2 is an exploded view of the prosthesis.

The present invention is desirably used in vascular prostheses having extremely thin walls, an example of which is shown in FIGS. 1 and 2. As is evident from FIG. 1, prosthesis 50 is a tubular vascular conduit having an extruded luminal sheath 52 and, optionally, also includes an extruded exterior sheath 54. Each sheath 52, 54 desirably has a thickness of less than or equal to about 250 µm, and more preferably less than or equal to about 200 µm, and more preferably less than or equal to about 125 µm.

In accordance with the subject invention, the sheaths 52, 54 are formed of expanded fluoropolymer, preferably ePTFE. In addition, the sheaths 52, 54, either one or both, are expanded from a green fluoropolymer tube 1, shown in FIG. 3. Preferably, the green tube 1 is formed of PTFE. In addition, as described in more detail below, the green tube 1 is formed by extrusion and, thus, includes a wall 2, which is seamless. The resulting sheaths 52, 54 are also, advantageously, seamless. Even though techniques had been developed in the prior art to seal seams in wrapped or rolled ePTFE tubes, the existence of such seams is not necessarily desirable and requires additional manufacturing steps as compared to tube extrusion techniques.

Figure 3:
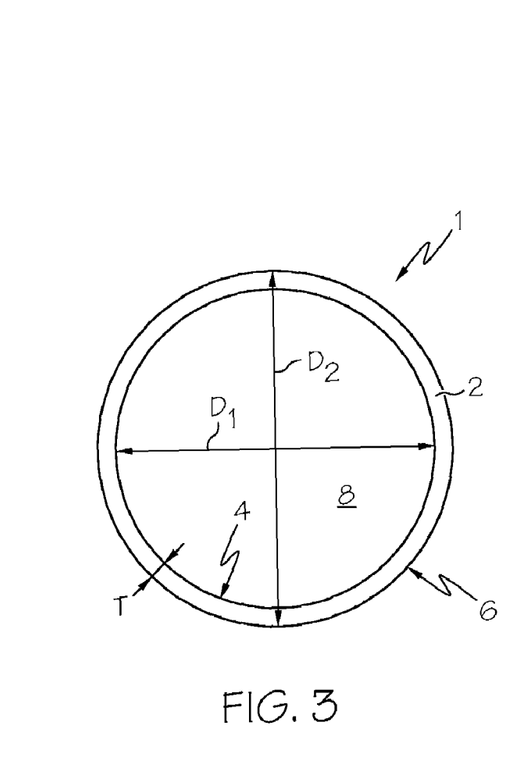
FIG. 3 is an end view of a green tube formed in accordance with the subject invention.

The wall 2 of the green tube 1 has a thickness T in the range of 250 µm and less. The thickness T is generally uniform throughout the wall 2 of a single extrudate. It is preferred that the thickness T be relatively uniform at generally all points in a single of the green tube 1. For example, with a green tube 1 having a wall thickness T in the range of 80-120 µm, it is desirable to limit variations in the wall thickness T to 5 µm or less. Other tolerances in the thickness T are possible. Preferably, the green tube 1 is cylindrical with an inner surface 4 of the wall 2 being formed about a diameter $D_1$ in the range of about 1-14 mm, and up to 35 mm, and an outer surface 6 being formed about a diameter $D_2$ in the range of about 1-14 mm, and up to 35 mm. Hollow lumen 8, with a relatively constant cross-section, is defined by the wall 2.

Prosthesis 50 may optionally further include a distensible member 56, preferably disposed between sheaths 52 and 54. As further shown in FIG. 2, distensible member 56 includes interstices 58 through which sheaths 52 and 54 adhere to one another at bonded regions 60. At least one of luminal sheath 52 and exterior sheath 54 may be flush with an extent of distensible member 56 or centered relative thereto to reveal at least one open portion of the distensible member thereby. Although both of sheaths 52 and 54 appear as extruded tubes that slide over distensible member 56 during assembly of prosthesis 50, either sheath 52, 54 may be a wrapped or rolled film or sheet having its opposing edges overlapped and secured to one another to form a tubular structure.

Assembly of prosthesis 50 is effected by first extruding a desired polymeric composition in a tubular profile, cutting such profile to a desired length, and working the cut profiles, (e.g., expanding; sintering) to obtain either or both of sheaths 52 and 54. Distensible member 56 is insertably retained within exterior sheath 54 such that an outer circumferential surface 56a of distensible member 56 contiguously contacts an interior circumferential surface 54a of sheath 54. Luminal sheath 52 is similarly insertably retained in distensible member 56 such that an outer surface 52a of sheath 52 contiguously contacts an interior circumferential surface 56b of distensible member 56. It is preferable that neither of sheath 52 or 54 be bonded to distensible member 56, thereby providing distensible member 56 with requisite freedom of movement without adversely affecting the integrity of sheaths 52 and 54.

Either or both of the luminal and exterior sheaths 52, 54 may be provided with an adhesive thereon that permits adherence of the polymeric sheaths to one another through interstices 58, thereby avoiding adherence of distensible member 56 to either or both of the sheaths 52, 54. The adhesive may be a thermoplastic adhesive and more preferably, a thermoplastic fluoropolymer adhesive such as FEP. A suitable adhesive provides a substantially integral and sealed prosthesis 50 without significantly reducing longitudinal and/or axial compliance. Alternatively, the two sheaths 52, 54 may be affixed by placing them under pressure and heating them above the softening or melting point of the constituent polymeric composition from which the tubes are formed to cause them to thermally adhere to one another.

As is known in the art, one or both of sheaths 52 and 54 may be impregnated with one or more therapeutic and pharmacological substances prior to implantation of the prosthesis 50 for controlled release over an extended duration. It is anticipated that prosthesis 50 can be partially or wholly coated with hydrophilic or drug delivery-type coatings which facilitate long-term healing of diseased vessels. Such a coating is preferably bioabsorbable, and is preferably a therapeutic agent or drug, including, but not limited to, anti-thrombogenic agents (such as heparin, heparin derivatives, urokinase, and PPack (dextrophenylalanine proline arginine chloromethylketone)); anti-proliferative agents (such as enoxaprin, angiopeptin, or monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-miotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D—Phe—Pro-Arg chloromethyl keton, an RGD peptide-containing compound, heparin, antithrombin compounds, platelet receptor antagonists, anti-thrombin anticodies, anti-platelet receptor antibodies, aspirin, prostaglandin inhibitors, platelet inhibitors and tick antiplatelet peptides); vascular cell growth promotors (such as growth factor inhibitors, growth factor receptor antagonists, transcriptional activators, and translational promotors); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vascoactive mechanisms. While the foregoing therapeutic agents have been used to prevent or treat various conditions, they are provided by way of example and are not meant to be limiting, as other therapeutic drugs may be developed which are equally applicable for use with the present invention.

Although a wide variety of distensible members may be used, FIG. 2 shows one particular distensible member 56, a stent, which may be employed in prosthesis 50. The particular stent shown in FIG. 2 is more fully described in commonly assigned U.S. Pat. No. 5,693,085 to Buirge et al. and the disclosure of U.S. Pat. No. 5,693,085 is incorporated by reference herein. The stent may be an intraluminally implantable stent formed of a metal such as stainless steel or tantalum, a temperature-sensitive material such as Nitinol or alternatively formed of a superelastic alloy or suitable polymer. Multiple struts 62 interconnect adjacent columns 64 to thereby define a plurality of the interstices 58 throughout the tubular configuration and further define a central open passage 66 therethrough. Struts 62 and columns 64 provide the distensible member 56 with a generally elongate tubular configuration which is radially expandable after implantation in a body vessel. The distensible member 56 may be formed by etching or cutting a pattern from a tube or, alternatively, formed by etching a pattern into a material or mold and depositing stent material in the pattern, such as by chemical vapor deposition or the like.

Although a particular stent construction is shown and described with reference to the present invention, various stent types and stent constructions may be employed in the present invention as the distensible member 56 for the use anticipated herein. Among the various useful distensible members 56 include, without limitation, self-expanding stents and balloon expandable stents. The stents may be capable of radially contracting as well. Self-expanding stents include those that have a spring-like action which causes the stent to radially expand or stents which expand due to the memory properties of the stent material for a particular configuration at a certain temperature. Other materials are of course contemplated, such as stainless steel, platinum, gold, titanium, tantalum, niobium, and other biocompatible materials, as well as polymeric stents.

The configuration of the distensible member 56 may also be chosen from a host of geometries. For example, wire stents can be fastened in a continuous helical pattern, with or without wave-like forms or zigzags in the wire, to form a radially deformable stent. Individual rings or circular members can be linked together such as by struts, sutures, or interlacing or locking of the rings to form a tubular stent.

To summarize, the prosthesis 50 may be a graft having the sheath 52, or optionally a multi-layer graft with the sheaths 52 and 54 and other optional layer(s) or, a stent-graft, with the sheath 52 (or optionally with the sheath 54 and other layer(s)), along with the distensible member 56. In a preferred stent-graft embodiment, the prosthesis 50 includes the sheaths 52, 54 and the distensible member 56 interposed therebetween. With the sheaths 52, 54 having wall thicknesses of 250 μm and less, the prosthesis 50 is exceptionally flexible and capable of navigating vasculature, yet sufficiently strong to properly function. The prosthesis 50 formed with the distensible member 56 interposed between the sheaths 52, 54 is preferably formed with a thickness in the range of 50-400 μm, although for certain applications, the prosthesis 50 may have a thickness as large as 1,000 μm. The wall thickness of the prosthesis 50, exclusive of the distensible member 56, is preferably about 120 μm or less.

Figure 4:
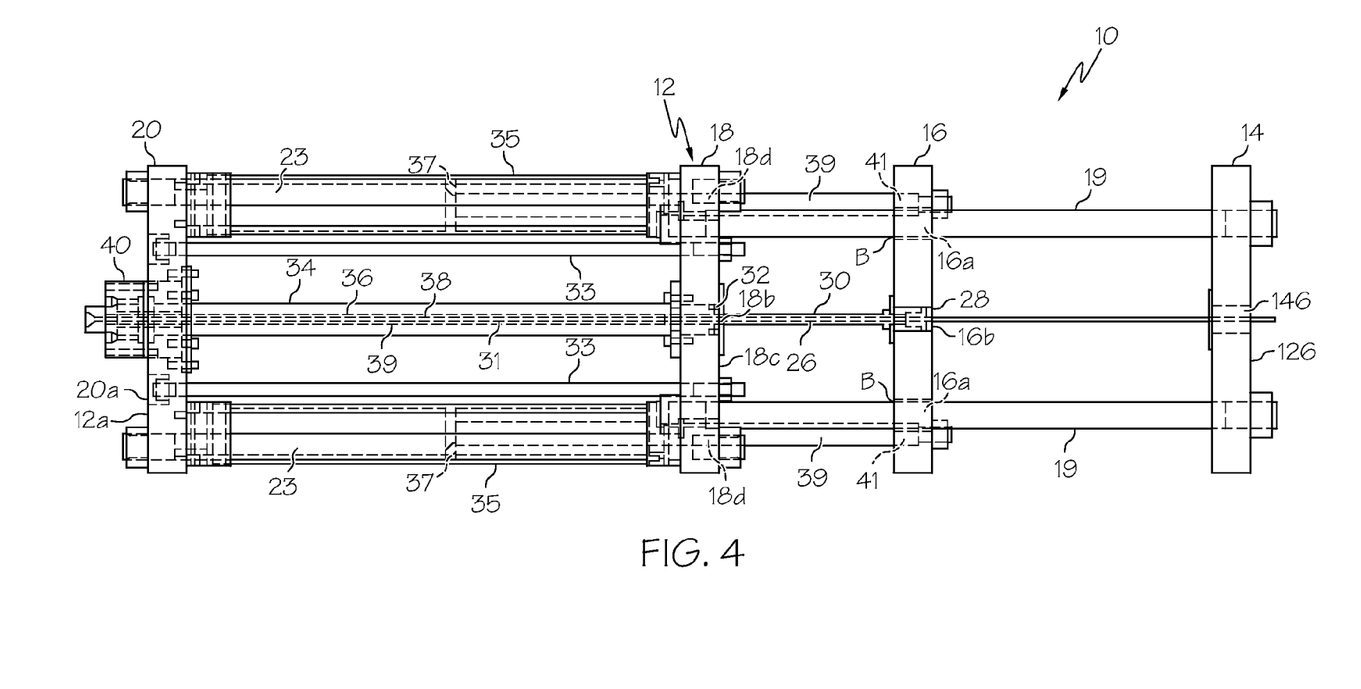
FIGS. 4 and 5 are top and side views on an extrusion apparatus which may be used for forming the green tube.
Figure 5:
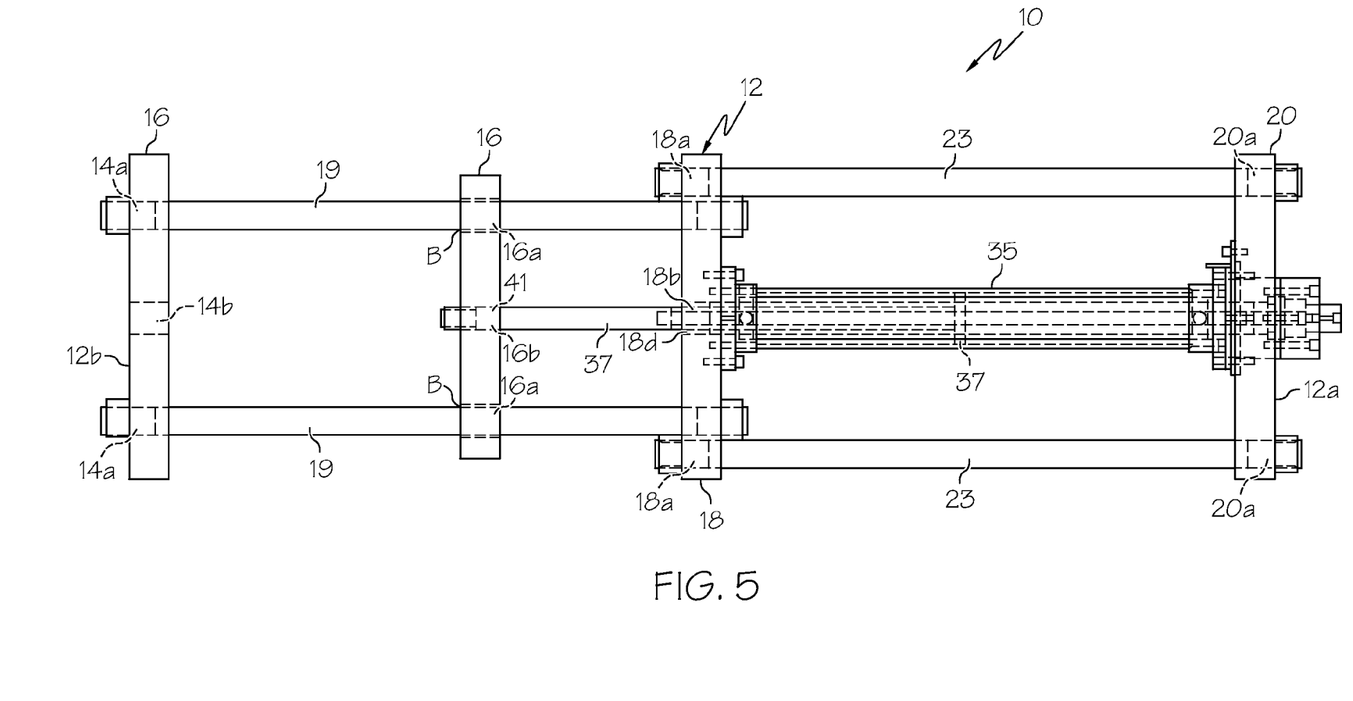

It is preferred that the green tube 1 used in forming the sheaths 52, 54 be extruded. With reference to FIGS. 4-5, an extruder 10 is depicted, the extruder being more completely described in copending application Ser. No. 10/012,825. The entire disclosure of copending application U.S. application Ser. No. 10/012,825 is incorporated herein by reference. An extruder 10 is a ram extruder formed for the extrusion of a pre-form (i.e., billet) of polymeric material into the green tube 1. Extruder 10 includes an extrusion mold assembly 12 (separately illustrated in FIG. 6) that provides a scaffolding for effective concentric support of requisite extruder elements thereby. Assembly 12, having a forward end 12a and a rearward end 12b, generally includes a series of platens including stationary platens 14 and 18 and traverse platen 16. Platens 14 and 18 are secured to one another in spaced alignment by a plurality of primary truss members 19.

Figure 6:
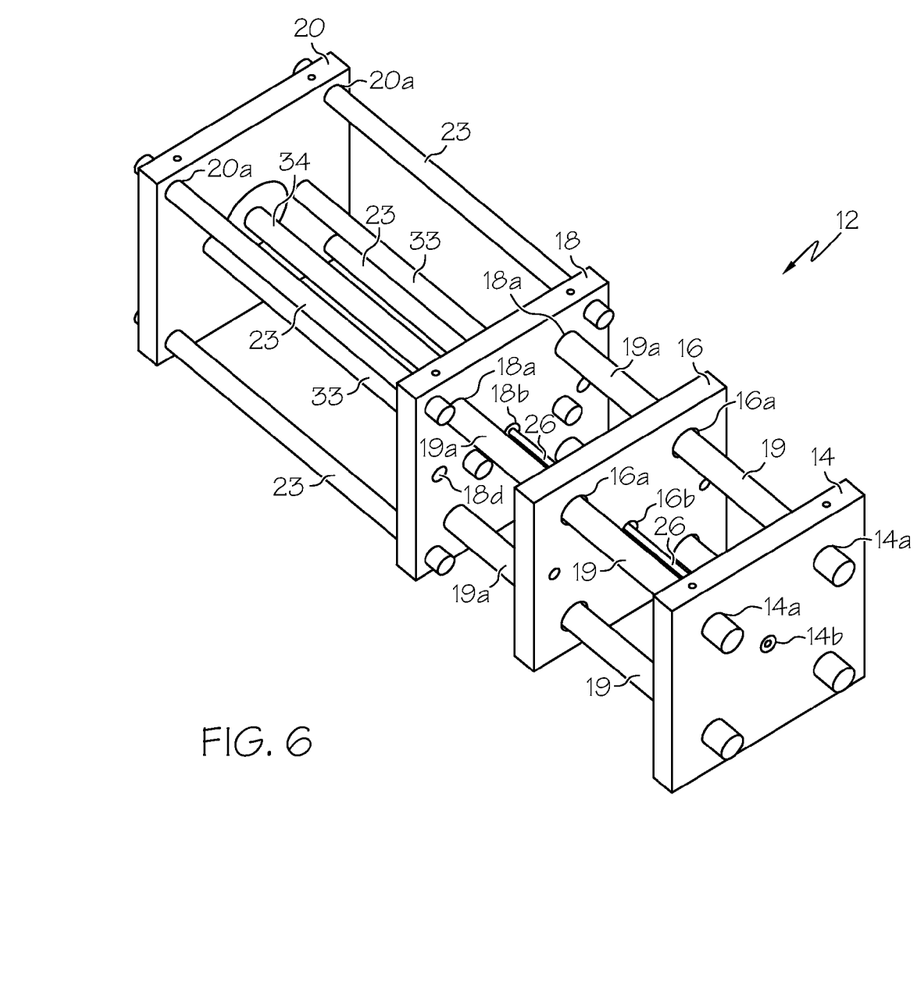
FIG. 6 is a perspective view of an extrusion mold assembly used with the extrusion apparatus.

As shown in FIGS. 4-6, four of the truss members 19 are utilized, although other quantities may be used. It is preferred that the platens 14, 18 be generally rectangular and that the truss members 19 be secured in orifices 14a, 18a respectively, in proximity to the corners of the platens 14, 18. Preferably, the truss members 19 are countersunk into the platens 14, 18, as more fully described below. With this arrangement, strong perimetric support for the platens 14, 18 may be provided which will maintain the platens 14,18 in a desired parallel arrangement.

The traverse platen 16 is formed with orifices 16a and is disposed in sliding engagement on central body portions 19a of the truss members 19 with the respective central body portions 19a passing through the orifices 16a. As is known to those skilled in the art, slide bearings B may be mounted in the orifices 16a to aid in sliding movement. It is critical to maintain parallelism between the traverse platen 16 and the platens 14, 18. Thus, it is desired that the slide bearings B be provided with relatively small clearances relative to the truss members 19, thus, minimizing twisting of the platen 16 during movement and maintaining parallelism.

Each of platens 14, 16 and 18 further includes a central aperture 14b, 16b, and 18b, respectively, therein to accommodate passage of annular extruder elements therethrough. Platens 14, 16 and 18 are notably coupled in parallel alignment so as to ensure corresponding parallel alignment therebetween for maintaining concentricity of the extruder elements throughout an extrusion cycle.

A front extruder plate 20 is also provided that similarly includes a plurality of orifices 20a defined therethrough to accommodate insertion of corresponding secondary truss members 23. Plate 20 also includes a central aperture 20b that accommodates passages of extruder members, as further described hereinbelow. Secondary truss members 23 are similarly formed to the truss members 19 and are secured to the plate 20 and the platen 16 through countersunk connections to maintain a parallel arrangement therebetween, also as described below. Truss members 23 not only provide support for plate 20, but they also ensure parallel arrangement of the plate 20 and the platens 14, 16, 18 and maintain coaxial alignment of apertures 14b, 16b, 18b and 20b.

Now referring particularly to FIGS. 4 and 5, a preferred configuration of concentric extruder elements may be described. Aperture 14b of plate 14 insertably accommodates a free extent of a guide rod 26 therethrough. Guide rod 26 is an elongate, generally cylindrical member traversing a length of assembly 12 in concentric relation with orifice 14b. Guide rod 26 is at least partially retained in such relation by guide rod bushing 28 that is annularly disposed in orifice 16b of traverse platen 16. Guide rod 26, is preferably hollow, but may be formed solid.

Guide rod 26 linearly extends in concentric relation through orifice 16b so as to be coaxially disposed within tubular ram 30 and more particularly in a bore 31 defined along a longitudinal axis thereof. Ram 30, along with guide rod 26, extend in coaxial relation through an elongate barrel 34 having a bore 36 defined therewithin. Ram bushing 32, that is positioned adjacent rear surface 18c of plate 18, circumscribes a periphery of ram 30 so as to maintain the coaxial relation of ram 30 relative to the barrel 34.

Ram 30 is coupled with piston 38 that is also disposed inside bore 36. An annular wiper element 39 is mounted onto the ram 30 and disposed adjacent to piston 38 so as to provide additional concentric support of the guide rod 26 in relation to the ram 30 and further in relation to the bore 36 during an extrusion operation. The wiper element 39 acts as a slide bearing between the barrel 34 and the guide rod 26 in providing support for the guide rod 26. There is tight contact between the guide rod 26, the wiper element 39, and the barrel 34.

Figure 7:
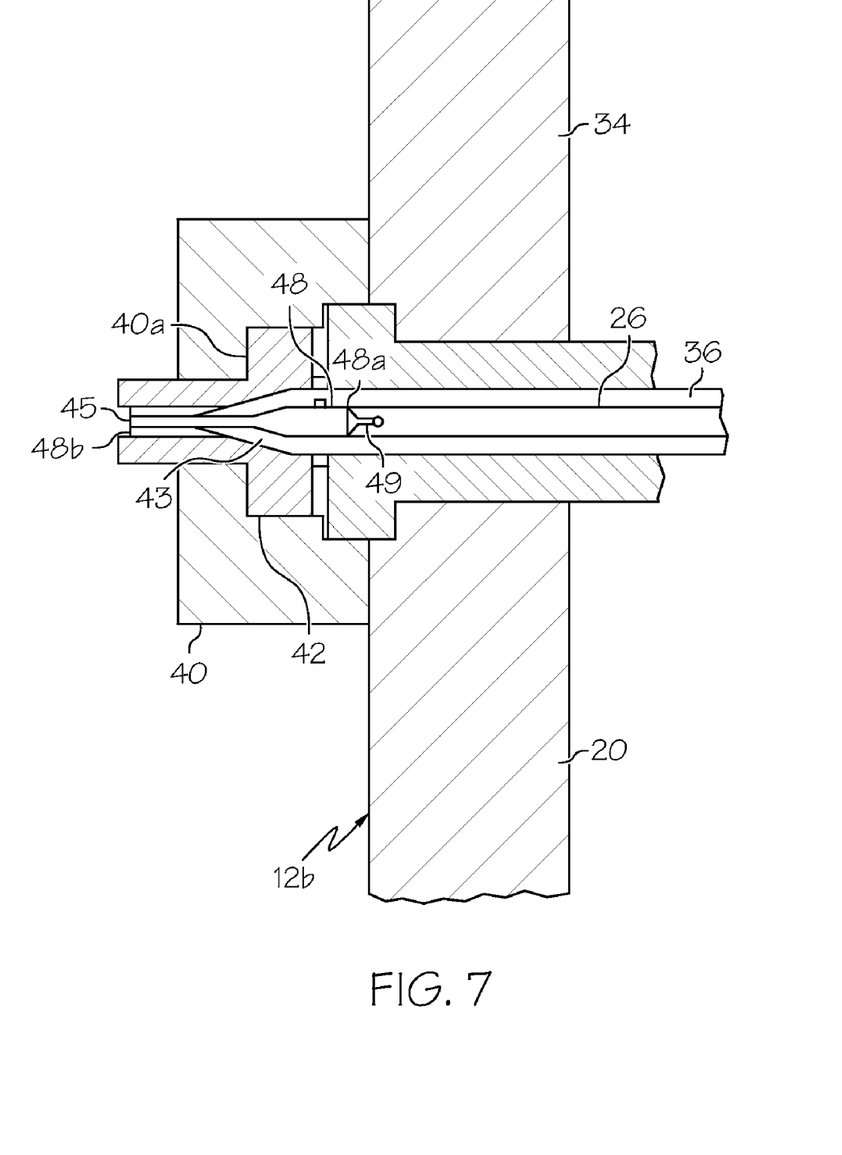
FIG. 7 is an enlarged view of a die and mandrel used with the extrusion apparatus.

As shown in FIGS. 4 and 5 and more particularly illustrated in the enlarged view of FIG. 7, a die mounting collar 40 having an opening 40a defined therethrough is annularly disposed about each of die 42 and a front extent of barrel 34 such that collar 40 concentrically supports the die 42 relative to the barrel 34. Die 42 includes a partially tapered extrudate passage 43 therethrough that terminates in an extrudate exit opening 45 at forward end 12b of assembly 12. The parameters of extrudate passage 43 are partially defined by smooth surface mandrel 48 about which a polymeric extrudate flows upon compression of a polymeric billet by ram 30.

The dimensions of the extrudate passage 43 dictate the dimensions of any resulting extrudate. A tip portion of the guide rod 26 defines the mandrel 48, wherein the mandrel 48 may be unitarily formed with the guide rod 26; or, more preferably, the mandrel 48 may be formed to be removable from the guide portion 26 with the mandrel 48 being concentrically supported by the remainder of the guide rod 26 by threads 49 or other securement means. It may be desired to allow for easy removal of the mandrel 48, to allow for maintenance and/or easy loading of a billet of polymeric material (as described below). The mandrel 48 may be flexible or flexibly connected to the guide rod 26 to allow for self-centering of the mandrel 48.

Referring again to FIG. 4, to further enhance secure support of the plate 20, tertiary truss members 33 may be mounted in proximity to the barrel 34. The tertiary truss members 33 are preferably countersunk into the plate 20 and the platen 14 in similar fashion as the truss members 19 described below.

Piston cylinders 35 are mounted to and extend between the front plate 20 and the platen 14 with drive pistons 37 being slidably disposed within the piston cylinders 35. Stems 39 of the drive pistons 37 extend from the cylinders 35 and through the platen 18 via orifices 18d. The stems 39 are sealed within the orifices 18d to prevent leakage from the cylinders 35. Ends 41 of the stems 39 are countersunk into the traverse platen 16 in similar fashion to the securement of the truss members 19 described below. Beneficially, the cylinders 35 add additional rigidity to the assembly 12, along with the countersunk connections with the traverse platen 16.

The cylinders 35 are charged with any driving medium known to those skilled in the art, such as hydraulic fluid or air. It is preferred that hydraulic fluid be used and that the fluid be steadily charged into the cylinders 35. As such the ram 30, via the traverse platen 16, can be steadily driven towards the die 42.

In operation, a ram extrusion process is initiated in extruder 10 by placing a billet or pre-form of a polymeric composition (not shown) into the bore 36 of the barrel 34. To facilitate placement of the billet, it is preferred that the die 42 be formed to be removed from the front plate 20. The billet can then be inserted into the barrel 34. Driving motion (i.e., via hydraulic action of drive pistons 37) transmitted to plate 16 advances plate 16 along truss members 19 toward plate 18, thereby advancing ram 30 through barrel 34. Advancement of ram 30 inures translational movement to piston 38 and wiper element 39 along guide rod 26, maintaining guide rod 26 in concentric alignment with ram 30, mandrel 48, extrudate passage 43 and opening 45. Further advancement of ram 30 exerts pressure upon the polymeric billet until the billet becomes a flowable extrudate. The extrudate flows through extrudate passage 43 along a smooth outer periphery of mandrel 48 to define a tubular profile thereby.

Figure 8:
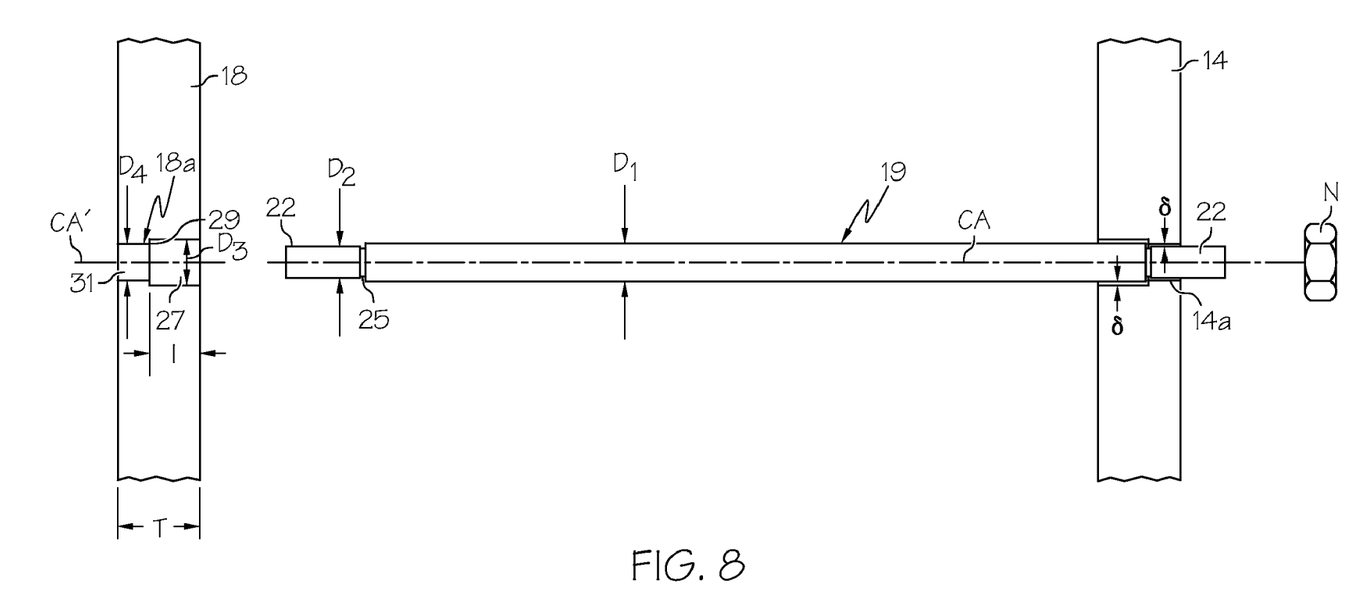
FIG. 8 is a side view of a truss member used with the extrusion apparatus.

As indicated, various connections in the extruder 10 are achieved with countersinking. To describe the countersinking connections, reference will be made to connections between the truss members 19 and the platens 14 and 18. It is to be understood that the other countersunk connections (i.e., the secondary truss members 23, the tertiary truss members 33, the piston stems 39) are formed dimensionally and structurally in the same fashion. With reference to FIG. 8, each of the truss members 19 is formed with the central body portion 19a, having a first diameter $D_1$, and end portions 22, each having a second diameter $D_2$ smaller than the diameter $D_1$. As a result of this structure, annular faces 25 are defined at the ends of the central body portion 19a which face outwardly. Preferably, the faces 25 are generally flat and perpendicularly disposed to a central longitudinal axis CA of the truss member 19. Correspondingly, the orifices 14a, 18a are each formed with a first diameter portion 27, an annular shoulder 29, and a reduced diameter portion 31. The first diameter portion 27 is formed with a diameter $D_3$ which is equal to the diameter $D_1$ plus a minimal clearance $\delta$, while the reduced diameter portion 27 is formed with a diameter $D_4$ which is equal to the diameter $D_2$ plus a minimal clearance $\delta'$. The clearances $\delta$, $\delta'$ are set to allow for assembly of the elements, but it is preferred to keep such clearances to a minimum, especially the clearance $\delta$. For example, with the diameter $D_1$ being equal to 2.0 inches (+0.0005/−0.0000 inches), the clearance $\delta$ is 0.001 inches (+0.0005/−0.000 inches) and thus the diameter $D_3$ is nominally 2.002 inches; whereas, with the diameter $D_2$ being equal to 1.75 inches (+0.01/−0.01), the clearance $\delta$ is 0.05 inches (+0.005/−0.005), and thus the diameter $D_4$ is nominally 1.85 inches. The tendency of the truss members 19 to shift will be a function of the clearances $\delta$, $\delta'$, and much more a function of the clearance $\delta'$. In addition, the extent the central body portion 21 extends into the first diameter portion 27 not only dictates the extent to which the truss members 19 can shift, but, also, dictates the extent to which the truss members 19 may buckle (i.e., cause lateral deflection of the central body portion 19a). It is preferred that the central body portion 19a extend a length 1 into the platen with the length 1 being at least 33.3% of the thickness T of the platen (e.g., 1 is at least 1 inch, where T is 3 inches). All of the countersunk connections are formed with the same dimensional relationships. It is further preferred that the shoulder 29 be generally flat and disposed perpendicularly to a central axis CA' of the respective orifice 14a, 18a.

In securing the truss members 19 to the platens 14, 18, the annular faces 25 are pressed into engagement with the shoulders 29, with the first diameter portions 27 partially accommodating the central body portions 19a and the end portions 22 extending through, and extending from, the reduced diameter portions 31. The bearing engagement of the truss members 19 with the orifices 14a, 18a, especially at the face 25/shoulder 29 interface and at the central body portion 21/first diameter portion 27 interface, constrains relative movement between the parts, including possible buckling of the truss members 19. To facilitate securing the truss members 19 to the platens 14, 18, the end portions 22 are at least partially threaded and nuts N are secured onto the end portions 22. Any securing means known to those skilled in the art may be utilized to secure the truss members 19 to the platens 14, 18.

It is further preferred that the platens 14, 16, 18 and the plate 20 be each formed of sufficient thickness so as to not deflect, twist, or shift relative to the truss members 19. As an exemplary embodiment, with the platens or plate being made of AISI 1060 steel, a thickness T of 3 inches may be provided.

With certain polymeric materials, e.g., PTFE, the tubular green extrudate collapses upon exiting the opening 45 when extruded at thicknesses of about 250 μm or less. To overcome this problem, the tip 48b of the mandrel is formed open and in communication with an open passage 48a extending through the mandrel 48. A stable medium is ejected from the tip 48b into the lumen of the extrudate to pressurize the lumen, and thus provide support. Preferably, the guide rod 26 is hollow and extends through the platen 18 allowing for a source of compressed air (80-100 p.s.i.g.) to be coupled thereto. The compressed air is urged the length of the guide rod 26 and through the mandrel 48. Consequently, the green extrudate is hollow and coreless upon formation.

Figure 9:
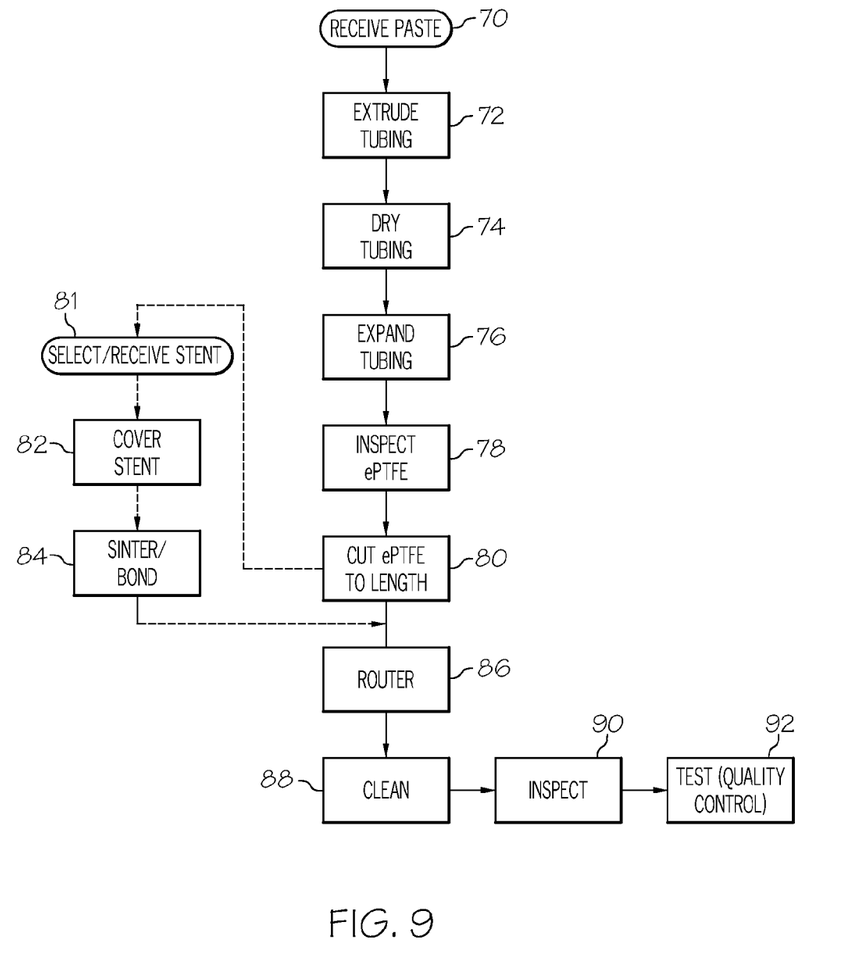
FIG. 9 is a flow chart setting forth a process for producing a prosthesis.

Referring to FIG. 9, a flow chart is set forth depicting an exemplary process for fabrication of various prostheses incorporating thin-walled extruded tubes. At initiating step 70, a polymeric paste is received (which may be provided in the form of a polymeric pre-form or billet). At block 72, the billet or paste is extruded into a green, extremely thin-walled tubular profile therefrom, such as, e.g., using the extruder 10. At block 74, the green extruded tubing is dried (preferably heated to remove any lubricants), and thereafter expanded (block 76) to derive ePTFE having a desired node and fibril configuration. The ePTFE tube is then inspected (block 78) and subsequently cut to one or more desired lengths (block 80). This ePTFE tube may be used as an endovascular prosthesis, such as a graft. If the prosthesis is to be a stent-graft, a stent is selected and received (block 81). ePTFE tubes are used to luminally or exteriorly (or both) cover the stent (block 82), and the covered stent is subjected to a sintering process such that the polymeric material fills interstices in the stent sidewall and adheres to itself to at least partially envelop the stent thereby; in addition, any adhesive disposed between the tubes is caused to activate (block 84). Regardless if the prosthesis is a stent or a stent-graft, it is subjected to a router (block 86), cleaned (block 88), inspected (block 90), and tested for quality control (block 92).

Notwithstanding the exceptional thinness of the extruded green tube disclosed herein, the thinness may even be further reduced by applying tension to the extrudate upon formation (i.e., pull the green tube at a rate exceeding the normal exit speed of the extrudate). This process would also reduce the diameter of the green tube.

An illustrative example of the formation of first a green tube, and then a prosthesis, is provided in the example below. It is emphasized that the values provided herein merely constitute an example of how the present inventive process can be completed, and that these values can be affected in view of material selection, desired tube thickness, piston velocity and related factors as described herein. It is therefore understood that any or all steps may be modified in sequence or duration to adapt to different applications.

EXAMPLE

ICI CD 123 resin is blended with isopar G lubricant at a ratio of 15.5. to 18% isopar by weight. The resin and lubricant are blended in a V-blender for approximately 15 minutes to form a paste thereby. A pre-former that compresses the paste into pre-form (i.e. cylindrical billets) is loaded with approximately 100 g of paste per pre-form. The paste is compressed into cylindrical pre-forms at hydraulic pressures ranging from 100 to 500 psi. Heat may be applied during compression in the range from about room temperature to about 125° F. It is preferred that the pre-forms be formed radially smaller than the bore 36 of the barrel 34. It is desirable to obtain a clearance of 0.03125" or less (as measured on diameter) between the pre-form and the barrel 34.

After removal of the pre-forms from the pre-former, the pre-forms are loaded into the extruder 10 and extruded as described above, forming an axially oriented green PTFE tube with wall thickness ranging from about 100 to 250 μm. The hydraulic pressures applied during extrusion range between about 200 and about 500 psi. The pressure applied by the piston 38 to the pre-form is in the range of about 800 to about 900 p.s.i.g. The desirable reduction ratio (i.e., ratio of pre-form cross-sectional area to cross-sectional area of extruded tube) is about 125 to about 350. During the extrusion, the extruder die and barrel are heated from about 77° F. to about 125° F. As the extrudate exits the extruder die, air at about 80-100 p.s.i.g. is injected into the lumen of the extrudate via the mandrel to maintain patency of the lumen. Upon take-up, the extrudate is lightly tensioned and cut into sections of predetermined length, at which point the extrudate is a "wet" green tube.

The resulting wet green tubes are placed on a tray and loaded into a hot air drying oven at about 125° F. for 2 hours. This process removes the isopar lubricant from the wet green tube, resulting in a dried PTFE tube (hereinafter "dry" green tube). The dry green tubes are thereafter cut to a required gage length that ranges from 2.0 to 20.0 cm and mounted on expansion chucks for elongation of the tubes. A mandrel is inserted into the lumen of each of the chucked green tubes; the mandrel providing a reproducible internal diameter for the desired expanded PTFE tube. Optionally, mandrels need not be used, wherein the dry green tubes are only loaded into expansion chucks.

The assembly of dry green tubes, expansion chucks and mandrels is loaded onto stretching trees that are used to elongate the PTFE tubes during an expansion process. The stretching trees and assorted assemblies are placed into an oven for expansion and sintering of the dry green tubes. The dry green tube assemblies are pre-heated to about 500° F. for 10 minutes, softening the PTFE for expansion. The pre-heated assemblies are then elongated between about 2000 and about 6000% of the original gage length to form expanded PTFE (ePTFE) tubes having a node and fibril microstructure. Velocities for the expansion range from about 2.0 to about 75.0 cm/sec, and accelerations during expansion range from about 500 to about 5000 cm/sec$^2$.

The ePTFE tubes are then sintered at a temperature of about 660° F. for 8-14 minutes so as to elevate the PTFE to its melting temperature. The ePTFE tubes are thereafter cooled to room temperature so as to preserve the dimensions and node/fibril microstructure of the tube. The cooled tubes are removed from the oven and the mandrels (if used) removed therefrom, revealing a complete ultra-elongate thin-walled ePTFE tube.

| Summary of ePTFE tubing: | |
|---|---|
| Wall thickness: | 10-250 μm |
| Longitudinal expansion: | 500-6000% |
| Internal diameters: | Preferred, 1-14 mm (optionally up to 35 mm) |

The present invention is thus particularly useful in producing a tubular, implantable vascular prosthesis (graft or stent-graft) of minimal outer diameter wherein the resultant tubing can be radially expanded up to five times, or more, of its original diameter. The prosthesis can be any used in connection with any of conventional and novel artificial grafts made of various materials and adapted in various configurations including straight, tapered or bifurcated and which may or may not be reinforced with rings, spirals or other reinforcements and which may or may not have one or more expandable stents incorporated into the graft at one or both ends or along its length. The prosthetic design of choice may be introduced into the vessel in any suitable way including, but not limited to, use of a dilator/sheath.

Where the graft is expandable and in tubular or sleeve form, the diametrical size of the graft may be enlarged into contiguous relationship with the inside surface of a vascular vessel via a balloon catheter. The tubular graft itself may comprise a biologically inert or biologically active anti-stenotic coating applied directly to the treated area of the remaining vascular inner surface to define a lumen of sufficient blood flow capacity. The graft, once correctly positioned and contiguous with the interior vascular wall, is usually inherently secure against inadvertent migration within the vessel due to friction and infiltration of weeping liquid accumulating on the inside artery wall. The length of the vascular graft preferably spans beyond the treated region of the vessel.

Various changes and modifications can be made to the present invention. It is intended that all such changes and modifications come within the scope of the invention as set forth in the following claims.

What is claimed is:

1. A process for forming an implantable prosthesis, comprising the steps of:
   extruding an extrudate consisting on a lubricant and PTFE to form a tubular member having a wall with an inner surface and an outer surface, a thickness being defined between said inner and outer surfaces in the range of about 250 μm or less at the exit of an extruder die used in the extruding, wherein said inner surface has a smooth inner surface having a single constant diameter;
   wherein a pressurized stable medium is injected into a lumen of said tubular member during extrusion to provide support thereof; and
   disposing a distensible member concentrically relative to said tubular member.

2. A process as in claim 1 further comprising:
   at least partially expanding said tubular member.

3. A process as in claim 2 further comprising extruding a fluoropolymer to form a second tubular member having a second wall with a second inner surface and a second outer surface, a second thickness being defined between said second inner and second outer surfaces, said second thickness being in the range of about 250 μm or less;
   at least partially expanding said second tubular member; and
   disposing said second expanded tubular member concentrically relative to said expanded tubular member.

4. A process as in claim 3, wherein said distensible member is interposed between said expanded tubular member and said second expanded tubular member.

5. A process as in claim 4, wherein said distensible member includes interstices, said expanded tubular member being bonded to said second expanded tubular member through said interstices.

6. A process as in claim 5, wherein said distensible member is non-bondedly disposed between said expanded tubular member and said second expanded tubular member.

7. A process as in claim 3, wherein said fluoropolymer is PTFE.

8. A process as in claim 3, wherein said second tubular member is expanded through about 500 to about 6000% of elongation.

9. A process as in claim 2, wherein said distensible member is at least partially recessed within said expanded tubular member.

10. A process as in claim 1, wherein said thickness being in the range of about 200 μm or less at the exit of the extruder die used in the extruding.

11. A process as in claim 10, wherein said thickness being in the range of about 125 μm or less at the exit of the extruder die used in the extruding.

12. A process as claim 1, wherein said tubular member is hollow upon extrusion.

13. A process as in claim 1, wherein said distensible member is disposed in contiguous contact with said inner surface.

14. A process as in claim 1, wherein said distensible member is disposed in contiguous contact with said outer surface.

15. A process as in claim 2, wherein said tubular member is expanded through about 500 to about 6000% of elongation.

16. A process as in claim 1, wherein tension is applied to said tubular member during extruding.

17. A process as in claim 1, wherein said thickness varies by 5 μm or less throughout the length of said tubular member.

18. A method of forming a stent-graft device comprising the steps of:
   forming an expandable fluoropolymeric tube from an extruded green fluoropolymer tube having a wall thickness of about 250 μm or less, said green fluoropolymer tube having an inner surface, said inner surface having a smooth inner surface having a single constant diameter;
   wherein a pressurized stable medium is injected into a lumen of said green fluoropolymer tube during extrusion of said green fluoropolymer tube to provide support thereof; and
   dispensing a distensible member concentrically thereabout.

19. A method as in claim 18 further comprising:
   dispensing a second expandable fluoropolymeric tube formed from an extruded green fluoropolymer tube having a wall thickness of about 250 μm or less about said distensible member.

20. A method as in claim 19, wherein said wall thickness of said second tube being about 200 μm or less.

21. A method as in claim 20, wherein said wall thickness of said second tube being about 125 μm or less.

22. A method as in claim 18 further including the step of joining together said tubes.

23. A method as in claim 22 wherein said joining includes the use of heat and pressure.

24. A method as in claim 22 wherein said joining includes the use of adhesive.

25. A method as in claim 18, wherein said wall thickness is about 200 μm or less.

26. A method as in claim 25, wherein said wall thickness is about 125 μm or less.

27. A process as in claim 1, wherein said inner surface has a substantially cylindrical cross-section.

28. A method as in claim 18, wherein said inner surface has a substantially cylindrical cross-section.

* * * * *